(12) United States Patent
Casola

(10) Patent No.: US 9,974,579 B2
(45) Date of Patent: May 22, 2018

(54) INTRAMEDULLARY DISTRACTION DEVICE

(71) Applicant: Robert Peter Casola, Naples, FL (US)

(72) Inventor: Robert Peter Casola, Naples, FL (US)

( * ) Notice: Subject to any disclaimer, the term of this patent is extended or adjusted under 35 U.S.C. 154(b) by 0 days. days.

(21) Appl. No.: 15/283,738

(22) Filed: Oct. 3, 2016

(65) Prior Publication Data

US 2018/0092673 A1   Apr. 5, 2018

(51) Int. Cl.
*A61B 17/72* (2006.01)
*A61F 2/38* (2006.01)
*A61F 2/42* (2006.01)
*A61B 17/68* (2006.01)

(52) U.S. Cl.
CPC ........ *A61B 17/72* (2013.01); *A61B 2017/681* (2013.01)

(58) Field of Classification Search
CPC ........ A61B 17/721782; A61B 17/7241; A61B 17/7291; A61B 17/7283; A61B 17/1717; A61B 17/7225; A61B 17/1725; A61B 17/4261; A61B 17/8061; A61B 17/1739; A61B 17/80; A61B 2017/681; A61B 2017/1782; A61F 2/4261; A61F 2/4241; A61F 2002/30062; A61F 2002/30331; A61F 2002/30481; A61F 2002/30507; A61F 2002/30538; A61F 2002/3054; A61F 2002/30622; A61F 2002/30774; A61F 2002/30777; A61F 2002/4264; A61F 2002/3085; A61F 2002/30332; A61F 2002/30405; A61F 2002/30433; A61F 2002/30471; A61F 2002/30494; A61F 2002/30578; A61F 2002/30607; A61F 2002/30614; A61F 2002/4677; A61F 2220/0016; A61F 2220/0025; A61F 2220/0033; A61F 2210/0004; A61F 2250/0006
USPC .............................. 606/60, 62–68, 98, 105; 623/20.14–20.24, 23.39, 23.47, 16.11
See application file for complete search history.

(56) References Cited

U.S. PATENT DOCUMENTS

| | | | |
|---|---|---|---|
| 8,454,706 B2* | 6/2013 | de Beaubien | A61F 2/36 623/23.39 |
| 9,445,912 B2* | 9/2016 | Oster | A61F 2/4261 |
| 2005/0102031 A1* | 5/2005 | Leonard | A61F 2/3836 623/20.21 |
| 2009/0171463 A1* | 7/2009 | Brehm | A61F 2/3836 623/20.14 |
| 2010/0130978 A1* | 5/2010 | Orbay | A61B 17/1782 606/62 |

(Continued)

*Primary Examiner* — Pedro Philogene
(74) *Attorney, Agent, or Firm* — Dunlap Bennett & Ludwig PLLC

(57) ABSTRACT

An intramedullary distraction device is provided. The device includes a first taper stem, a second taper stem, a first coupler and a second coupler. The first coupler includes a top end and a bottom end. The first taper stem is secured to the top end of the first coupler. The bottom end of the first coupler forms an inner sidewall. The second coupler includes a bottom end and a top end. The second taper stem is secured to the bottom end of the second coupler. The top end of the second coupler includes an inner sidewall that mates with the inner sidewall of the first coupler. A connector releasably connects the first coupler to the second coupler.

8 Claims, 4 Drawing Sheets

(56) References Cited

U.S. PATENT DOCUMENTS

2011/0208315 A1\* 8/2011 Anapliotis ............ A61F 2/3836
623/20.24

\* cited by examiner

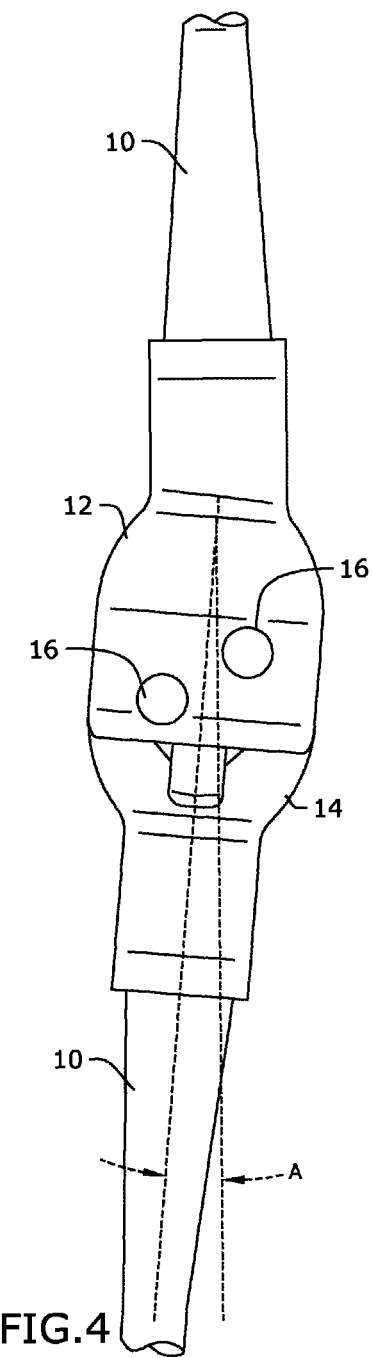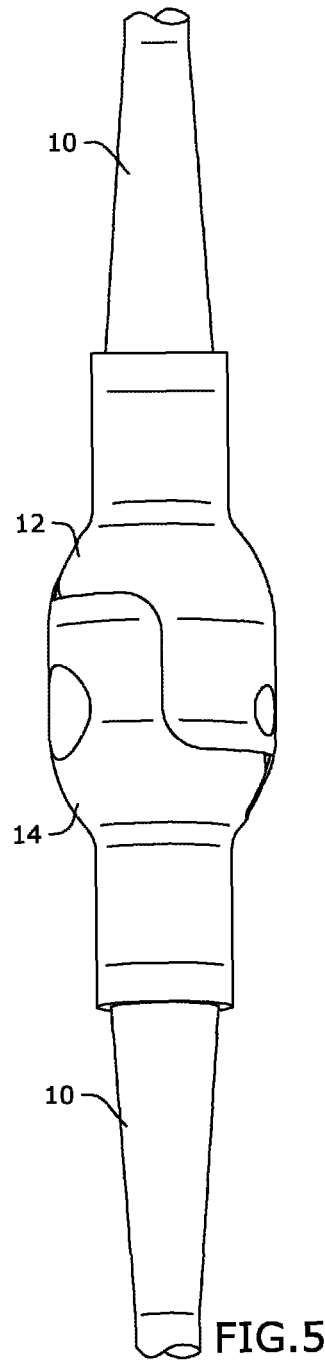

INTRAMEDULLARY DISTRACTION DEVICE

BACKGROUND OF THE INVENTION

The present invention relates to distraction of a joint and, more particularly, to an intramedullary distraction device.

During the implantation of an antibiotic spacer into the knee joint for infection treatment, the knee joint must be stabilized. Currently, to stabilize the knee joint, cement or other devices may be used. However, existing athrodesis devices are very costly, cause extensive bone loss and require excessive time for insertion and removal.

As can be seen, there is a need for a device for stabilizing the knee joint that is quick and easy to insert and remove.

SUMMARY OF THE INVENTION

In one aspect of the present invention, an intramedullary distraction device comprises: a first taper stem; a first coupler comprising a top end and a bottom end, wherein the first taper stem is secured to the top end and the bottom end forms an inner sidewall; a second taper stem; a second coupler comprising a bottom end and a top end, wherein the second taper stem is secured to the bottom end and the top end forms an inner sidewall that mates with the inner sidewall of the first coupler; and a connector releasably connecting the first coupler to the second coupler.

These and other features, aspects and advantages of the present invention will become better understood with reference to the following drawings, description and claims.

BRIEF DESCRIPTION OF THE DRAWINGS

FIG. 4 is a detail front view of an embodiment of the present invention;

FIG. 5 is a detail side view of an embodiment of the present invention;

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention includes an intramedullary distraction device for knee joint stabilization. The present invention may be used for stabilizing and distracting the knee joint internally for implantation of an antibiotic spacer for infection treatment. The present invention may compliment other intramedullary stems utilizing a low profile articulating device that can fit within the knee joint space, allow for antibiotic spacer implementation and then is easily removed.

The present invention includes a tibial morse taper stem that seats into a tibial coupler. The tibial morse taper stem is then seated into the proximal tibial bone. A flange of the tibial morse taper stem is seated posteriorly in the knee joint space. A femoral morse taper stem seats into a femoral coupler. The femoral morse taper stem is then seated into the distal femoral bone. A flange of the femoral morse taper stem is seated anteriorly in the knee joint space. The couplers are engaged in a closed book fashion. Hex-head screws may be placed into screw ports. A torque wrench is used to engage for insertion of the screws. Antibiotic cement can be placed around distraction device. Prior to insertion, the knee joint is flexed and reamed to accept the stem and each coupler. About a 4.5 cm separation between the bone interfaces is present for acceptance of the prosthesis in its entirety.

Each coupler with the intramedullary stem implant can be inserted individually with the knee inflection minimizing bone loss and joint separation. Upon engagement, the couplers lock the knee into a full extension and are secured with two locking screws. This transforms the knee into a stable rigid entity with intramedullary fixation to prevent migration, rotation and settling. The present invention includes an easy configuration that allows easy engagement and disengagement for its removal.

The present invention may be used in other areas where bone fixation may be necessary, either permanently or temporarily, to provide rigidity to a single bone or to bones of a joint, either weight bearing or non-weight bearing.

Figure 1:
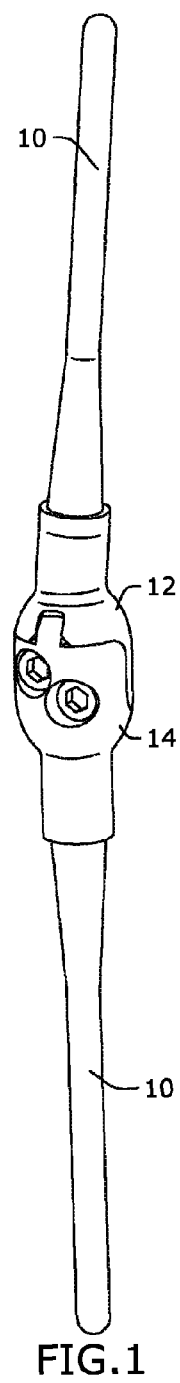
FIG. 1 is a perspective view of an embodiment of the present invention.
Figure 2:
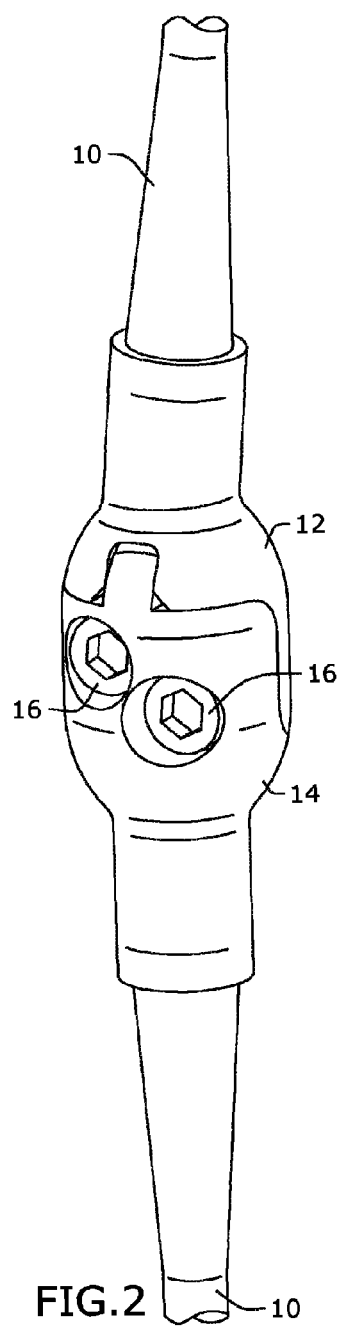
FIG. 2 is a detail perspective view of an embodiment of the present invention.
Figure 3:
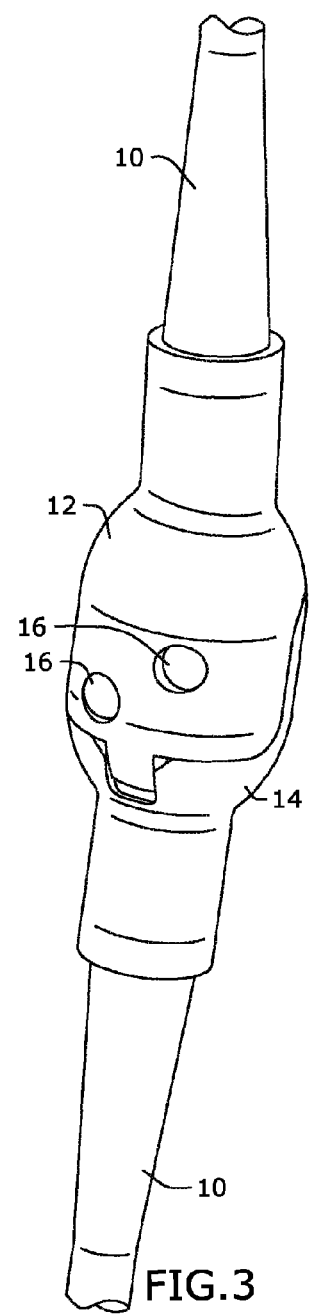
FIG. 3 is a detail perspective view of an embodiment of the present invention rotated 180 degrees along the vertical axis of FIG. 2.
Figure 6:
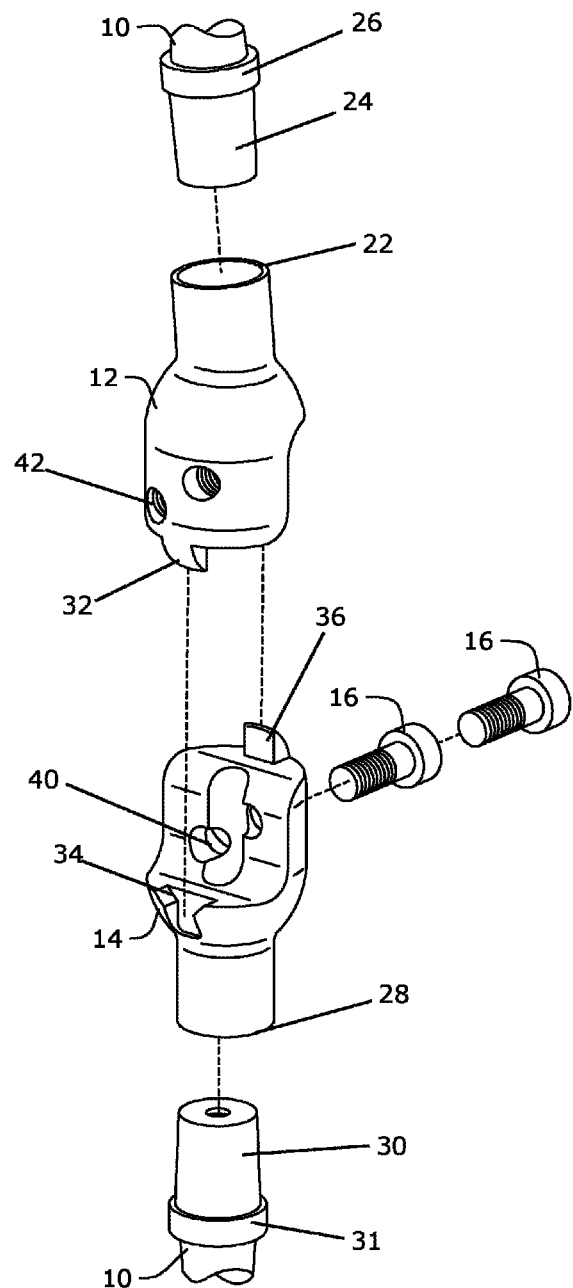
FIG. 6 is an exploded view of an embodiment of the present invention.
Figures 7, 8:
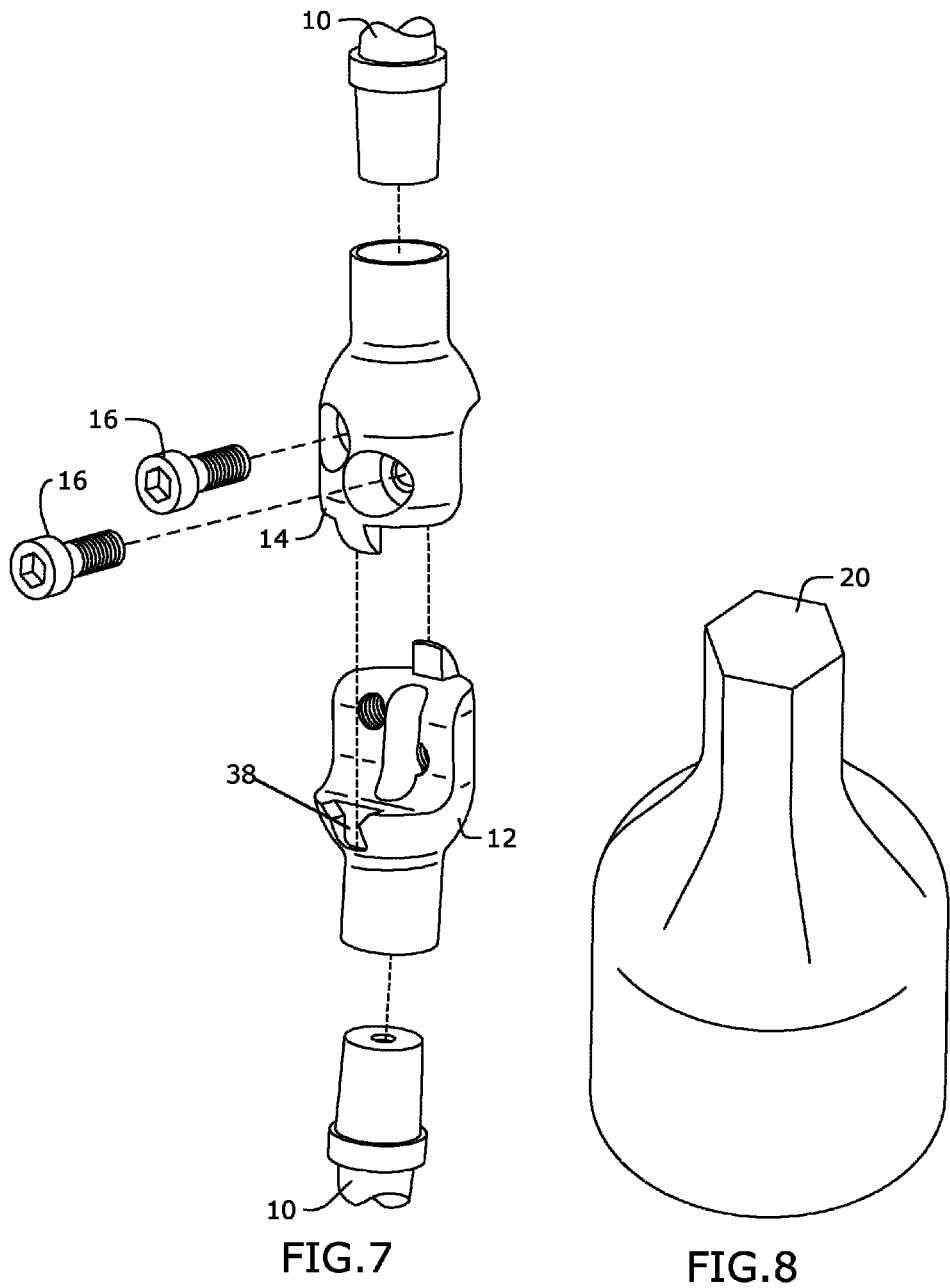
FIG. 7 is an exploded view of an embodiment of the present invention rotated 180 degrees along the horizontal axis of FIG. 6.
FIG. 8 is a perspective view of a component of the present invention.

Referring to FIGS. 1 through 8, the present invention includes an intramedullary distraction device. The device includes a first taper stem 10, a second taper stem 10, a first coupler 12 and a second coupler 14. The first coupler 12 includes a top end and a bottom end. The first taper stem 10 is secured to the top end of the first coupler 12. The bottom end of the first coupler 12 forms an inner sidewall. The second coupler 14 includes a bottom end and a top end. The second taper stem 10 is secured to the bottom end of the second coupler 14. The top end of the second coupler 14 includes an inner sidewall that mates with the inner sidewall of the first coupler 12. A connector 16 releasably connects the first coupler 12 to the second coupler 14.

In certain embodiments, the intramedullary distraction device is used to lock the knee joint. In such embodiments, the first taper stem 10 is the tibial morse taper stem and is sized to fit within a medullary cavity of a proximal tibial bone. The second taper stem 10 is the femoral morse taper stem and is sized to fit within a medullary cavity of a distal femoral bone. The first coupler 12 is the tibial coupler and the second coupler 14 is the femoral coupler. Further, in such embodiments, the first taper stem 10 and the second taper stem 10 are disposed at a valgus angle (V) relative to one another. For example, the first coupler 12 and the second coupler 14 are secured together at an angle forming the valgus angle (A). Alternatively, one or both of the couplers 12, 14 are bent.

The first taper 10 may be removably attached to the first coupler 12 and the second taper stem 10 may be removably attached to the second coupler 14. In such embodiments, the top end of the first coupler may form a top slot 22. The first taper stem 10 may include a first shaft 24 that slidably engages with the top slot 22. The first shaft 24 may include a flange 26 that abuts a rim forming the entrance of the top slot 22. The bottom end of the second coupler 14 may form a bottom slot 28. The second taper stem 10 may include a second shaft 30 that slidably engages with the bottom slot 28. The second shaft 30 may include a flange 31 that abuts a rim forming the entrance of the bottom slot 28.

In certain embodiments, the inner sidewall of the first coupler 12 contours with the inner sidewall of the second coupler 14. In certain embodiments, the inner sidewall of the first coupler 12 may include an S-shape and the inner surface of the second coupler 14 may include a mirrored S-shape of the first coupler 12, and may thereby nest together. In certain embodiments, a first tooth 32 protrudes beyond the bottom end of the first coupler 12 and a first slot 34 is formed at a bottom portion of the inner sidewall of the second coupler 14. The first tooth 32 locks into the first slot 34. In certain embodiments, a second tooth 36 protrudes beyond the top end of the second coupler 14 and a second slot 38 is formed at a top portion of the inner sidewall of the first coupler 12. The second tooth 36 locks into the second slot 38.

The connector 16 of the present invention may include threaded hex bolts operable to be turned by a hex tool 20. In such embodiments, one of the first coupler 12 and the second coupler 14 includes at least one opening 40 and the other of the first coupler 12 and the second coupler 14 includes at least one threaded opening 42 aligned with the at least one opening 40. The threaded bolt may run through the aligned openings and engage the threaded opening 42, thereby connecting the first coupler 12 and the second coupler 12 together. The opening 40 and the threaded opening 42 are formed through an outer sidewall and the inner sidewall of the first and second couplers 12, 14. In certain embodiments, the at least one opening 40 is a pair of openings 40 and the at least one threaded opening 42 is a pair of threaded openings 42. In such embodiments, the at least one threaded bolt is a pair of threaded bolts.

It should be understood, of course, that the foregoing relates to exemplary embodiments of the invention and that modifications may be made without departing from the spirit and scope of the invention as set forth in the following claims.

What is claimed is:

1. An intramedullary distraction device comprising:
   a first taper stem;
   a first coupler comprising a top end and a bottom end, wherein the first taper stem is secured to the top end and the bottom end forms an inner sidewall comprising a top horizontal portion, a vertical portion and a bottom horizontal portion, wherein a first slot is formed above the top horizontal portion;
   a second taper stem;
   a second coupler comprising a bottom end and a top end, wherein the second taper stem is secured to the bottom end and the top end forms an inner sidewall comprising a top horizontal portion, a vertical portion and a bottom horizontal portion, wherein a first tooth extends beyond the top horizontal portion, wherein the inner sidewall of the second coupler mates with the inner sidewall of the first coupler and the first tooth interlocks with the first slot; and
   a connector releasably connecting the first coupler to the second coupler.

2. The device of claim 1, wherein the first taper stem is sized to fit within a medullary cavity of a proximal tibial bone, and the second taper stem is sized to fit within a medullary cavity of a distal femoral bone.

3. The device of claim 1, wherein the top end of the first coupler comprises a top slot and the first taper stem comprises a first shaft inserted into the top slot, wherein the bottom end of the first coupler comprises a bottom slot and the second taper stem comprises a second shaft inserted into the slot.

4. The device of claim 1, wherein the first taper stem and the second taper stem are disposed at a valgus angle relative to one another.

5. The device of claim 1, wherein the first coupler comprises a second tooth extending beyond the bottom horizontal portion of the first coupler, and the second coupler comprises a second slot formed beneath the bottom horizontal portion of the second coupler, wherein the second tooth interlocks with the second slot.

6. The device of claim 1, wherein one of the first coupler and the second coupler comprises at least one opening and the other of the first coupler and the second coupler comprises at least one threaded opening aligned with the at least one opening, wherein the connector is at least one threaded bolt.

7. The device of claim 6, wherein the opening and the threaded opening are formed through an outer sidewall and the inner sidewall of the first and second couplers.

8. The device of claim 6, wherein the at least one opening is a pair of openings and the at least one threaded opening is a pair of threaded openings, wherein the at least one threaded bolt is a pair of threaded bolts.

* * * * *